US011726061B2

(12) United States Patent
De Oliveira E Silva et al.

(10) Patent No.: US 11,726,061 B2
(45) Date of Patent: Aug. 15, 2023

(54) PROBE ELEMENT AND METHODS FOR SEPARATION AND SENSING OF ANALYTES CONTROLLED BY TEMPERATURE

(71) Applicant: UNIVERSIDADE DE AVEIRO, Aveiro (PT)

(72) Inventors: Nuno Joao De Oliveira E Silva, Oporto (PT); Rui Pedro Oliveira Silva, Fafe (PT)

(73) Assignee: UNIVERSIDADE DE AVEIRO, Aveiro (PT)

( * ) Notice: Subject to any disclaimer, the term of this patent is extended or adjusted under 35 U.S.C. 154(b) by 781 days.

(21) Appl. No.: 16/609,116

(22) PCT Filed: May 24, 2018

(86) PCT No.: PCT/IB2018/053697
§ 371 (c)(1),
(2) Date: Oct. 28, 2019

(87) PCT Pub. No.: WO2018/215970
PCT Pub. Date: Nov. 29, 2018

(65) Prior Publication Data
US 2020/0232946 A1    Jul. 23, 2020

(30) Foreign Application Priority Data

May 26, 2017    (PT) ........................................ 110107

(51) Int. Cl.
G01N 27/72    (2006.01)
G01N 33/58    (2006.01)
H01F 1/00    (2006.01)

(52) U.S. Cl.
CPC ........... *G01N 27/72* (2013.01); *G01N 33/587* (2013.01); *H01F 1/0045* (2013.01)

(58) Field of Classification Search
CPC ...... G01N 27/72; G01N 33/587; G01N 27/00; H01F 1/0045
See application file for complete search history.

(56) References Cited

U.S. PATENT DOCUMENTS 6,844,202 B2    1/2005  Prinz et al.
7,696,548 B2    4/2010  Wang et al.
(Continued)

FOREIGN PATENT DOCUMENTS

WO    2005010542 A2    2/2005
WO    WO-2018156920 A1 *  8/2018    ........... H01F 1/0054

OTHER PUBLICATIONS

Wahajuddin et al., "Superparamagnetic iron oxide nanoparticles: magnetic nanoplatforms as drug carriers." International journal of nanomedicine vol. 7 (2012): 3445-71.doi:10.2147/IJN.S30320 (Year: 2012).*

(Continued)

*Primary Examiner* — Daniel R Miller
(74) *Attorney, Agent, or Firm* — Lucas & Mercanti, LLP (57) ABSTRACT

A probe element for separation and sensing of analytes of interest controlled by temperature is provided. The probe element includes at least one magnetic crystal and one or more types of capping agents. The capping agent can have stabilizing and or anchoring functions. The magnetic crystal produces a stable magnetic field at the temperature of interest for sensing or separation. The stable magnetic field can be controlled by temperature and the probe can be integrated in a sensing and or separation device and process.

29 Claims, 5 Drawing Sheets

(56) References Cited

U.S. PATENT DOCUMENTS 7,906,345 B2   3/2011   Wang et al.
9,121,887 B2   9/2015   Wang et al.
2009/0104707 A1   4/2009   Wang et al.

OTHER PUBLICATIONS

Zhang et al., Fe3Se4 Nanostructures with Giant Coercivity Synthesized by Solution Chemistry, Chemistry of Materials 23 (16), 3769-3774, 2011 (Year: 2011).*
Wang et al., Bifunctional Nanoparticles with Magnetization and Luminescence, The Journal of Physical Chemistry C 113 (10), 2009 (Year: 2009).*
Suda et al., "Reversible Photoswitching of Ferromagnetic FePt Nanoparticles at Room Temperature", J. Am. Chem. Soc., 2007, vol. 129, No. 17, pp. 5538-5543.
Solano et al., "Facile and efficient one-pot solvothermal and microwave-assisted synthesis of stable colloidal solutions of MFe2O4 spinel magnetic nanoparticles", .J Nanopart Res., 2012, vol. 14, No. 8, pp. 1-15.
Sharma et al., "Synthesis and self-assembly of monodisperse CoxNi100-x (x=50,80) colloidal nanoparticles by homogenous nucleation", Journal of Colloid and Interface Science, 2010, vol. 351, No. 2, pp. 323-329.
Zhang et al., "Controlled synthesis and anomalous magnetic properties of relatively monodisperse CoO nanocrystals", Nanotechnology, 2005, vol. 16, No. 10, pp. 2288-2294.
International Search Report and Written Opinion for International Application No. PCT/IB2018/053697 (17 Pages) (dated Nov. 11, 2018).

* cited by examiner

PROBE ELEMENT AND METHODS FOR SEPARATION AND SENSING OF ANALYTES CONTROLLED BY TEMPERATURE

CROSS-REFERENCE TO RELATED APPLICATIONS

This application is a 371 of PCT/IB2018/053697 filed May 24, 2018, which claims the benefit of Portuguese Patent Application No. 110107 filed May 26, 2017, both applications are incorporated herein by reference.

TECHNICAL FIELD

This application relates to probes and methods for separation and sensing of analytes.

BACKGROUND ART

Magnetic particles, nanoparticles and beads are currently used as probes for magnetic detection of a wide range of analytes, as described, for instance in U.S. Pat. No. 7,906,345, WO/2005/010542, US20090104707, U.S. Pat. Nos. 7,696,548, 6,844,202, 9,121,887, references therein [1-6] and in the literature [7-10]. Almost all references consider the use of paramagnetic, superparamagnetic or any other kind of magnetic particles, nanoparticles and beads that appear "non-magnetic" in the absence of a magnetic field [1, 3-6]. The reason is that particles that appear "magnetic" in the absence of an external magnetic field (in other words particles with a remanent magnetization, i. e. particles able to create a magnetic field in the absence of an external magnetic field) tend to agglomerate, which makes their use in assays difficult and less reliable [1,3,6]. The exceptions that consider possible the use of particles that appear "magnetic" in the absence of an external magnetic field just ignore the problem of agglomeration and do not present a solution for it [2].

The use of particles that appear "non-magnetic" does not mean that agglomeration will not occur. In fact, "non-magnetic" particles, nanoparticles and beads stable in normal conditions have sometimes tendency to aggregate when in the presence of an external field. The presence of such field is mandatory during detection, since in its absence the particles appear "non-magnetic". The state of art mitigates this problem of in-field aggregation by using smaller external fields during the assay and by improving surface modification [3]. This mitigation comes at the expense of signal to noise ratio since at smaller fields the magnetization induced in the particles is (proportionally) smaller and better stabilization implies bulky ligands and larger distances between particles and sensors.

The use of an external field during reading is, by itself, a source of errors. As this field sums to the field created by the particles, extra design is needed. This extra design typically includes the use of an alternating (perpendicular) magnetic field [1-3] or the use of multiple readers [11].

Therefore, the state of the art present the following problems and constrains:

Aggregation of Nanoparticles Possessing a Permanent Magnetic Field:

Magnetic nanoparticles able to create a permanent magnetic field (nanoparticles with a remanent magnetization) are systematically excluded from sensing and separation devices due to their tendency to aggregate. Aggregation impacts negatively their rheology, their interaction with analytes and their signal, since the magnetic field can be enclosed in loops of particles making the detectable signal low. In this sense, superparamagnetic nanoparticles and beads (i. e. nanoparticles creating a zero magnetic field in the absence of an external field) are considered the best choice for sensing and separation and have been developed to that aim.

Lack of a Permanent Magnetic Field (Permanent Remanent Magnetization or Moment) in Superparamagnetic Beads:

Although applied in sensing, superparamagnetic nanoparticles and beads need the presence of an external field to be detected. This external field, however, interacts with the reader, decreasing the sensitivity of the device. Perpendicular geometries and multiple readers are used to mitigate this problem [11]. However, cross-talking between different directions in the magnetic field readers always take place, leading to inaccuracy and errors. Also, by using perpendicular geometries, the whole field created by the nanoparticle is not detected but just a smaller weaker component, a fringe field [7], meaning that the full potential of the magnetic signal is not explored.

One Analyte Magnetic Separation Per Step:

Separation using magnetic nanoparticles and beads explores the force exerted by a magnetic field gradient on the nanoparticles/beads. This force depends mainly on viscosity, magnetic susceptibility and volume. Separation is often used as a way to concentrate an analyte of interest before its detection. Concentrate should be understood as the selective capture of the analyte of interest or selective elimination of non-wanted materials or media, resulting in a product where the analyte of interest has an enhanced concentration. In practice, a batch of homogeneous nanoparticles/beads is used and a complete separation process includes an incubation step, where chemically selective attachment between nanoparticles/beads and an analyte of interest occurs, followed by the application of a magnetic field gradient to separate and concentrate said analyte. Such concentration step assumes a special relevance in ultra-sensitive microfluidic-based devices, as most of point-of-care devices being developed, due to the low diffusion of molecules. Consequently, one must choose to use high volume of sample or wait a longer period of time in order to achieve the equilibrium specially in high diluted analytes (below nanomolar range). Both the amount of sample and time are crucial elements in point-of-care devices, being the absence of a concentration step (such as that provided by magnetic separation) a major drawback in these devices.

However, current magnetic separation methods and devices are useful to separate one analyte per incubation step and multiple incubation/separation steps are needed in the case where several analytes are being detected in the same device.

In this view, it would be desirable to have probe elements that (i) do not need an external field bias or tickling field to be detected, (ii) do not aggregate, and (iii) multiple analytes could be separated and concentrated after one incubation step.

SUMMARY

The present application relates to probes and methods for separation and sensing of analytes comprising a probe element with at least one magnetic crystal and at least one type of capping agent. The magnetic crystal provides a controllable remanent magnetization creating a controllable magnetic field to be sensed.

In an embodiment the magnetic crystal produces a magnetic field in the absence of an external field at a temperature of use.

In an embodiment the magnetic crystal further produces a magnetic field in a well-defined direction and in its opposite direction.

In another embodiment the intensity of the magnetic field produced by the magnetic crystal changes by a temperature change.

In an embodiment the aggregation of the probe element is controlled by the magnetic field created by the magnetic crystal of the probe element, which in turn is controlled by temperature change.

In another embodiment a second magnetic crystal does not produce a magnetic field in the absence of an external field at a temperature of use.

In an embodiment the second magnetic crystal generates heat by the application of an external alternating magnetic field.

In another embodiment at least one of the capping agents behaves as an anchoring agent.

In one embodiment at least one of the capping agents acts as a stabilizing agent.

In another embodiment the capping agents are organic molecules/coatings, inorganic molecules/coatings, organic-inorganic coatings or a mixture thereof.

In another embodiment at least one of the capping agents is luminescent.

The present invention further includes a device comprising at least one probe element, at least one analyte of interest, at least one temperature controller, at least one magnetic field reader, and at least one minute magnetic field source that does not interact with the said reader.

In an embodiment the analytes of interest are cells, cell biomarkers, synthetic biomarkers, synthetic biomarkers composites, biomolecules, exosomes, vesicles, organic molecules, inorganic molecules, molecular clusters, nanoparticles.

In an embodiment the temperature controller of the device comprises a heating element, a temperature sensor, and a feedback and/or feedforward controller.

In another embodiment the heating element is the probe element that absorbs energy from an external source and converts this energy into heat.

In an embodiment the probe element is coupled or embedded into the magnetic field reader.

In another embodiment the magnetic field reader is a fluxgate sensor.

In an embodiment the fluxgate sensor is a miniaturized unit.

In another embodiment the magnetic field reader is a magnetoresistive sensor.

In another embodiment the magnetic field reader is a tip-based device.

In an embodiment the tip-based device is an atomic force device.

In another embodiment the tip of the atomic force device has a magnetic crystal.

In an embodiment the magnetic field source is a coil at a distance from the reader.

In an embodiment the magnetic field source is a permanent magnet at a distance from the reader.

In another embodiment the magnetic field source is embedded in the magnetic field reader.

In an embodiment the reader is at a distance from a shielded magnetic field source.

The present application also includes a process of analyte determination comprising an inlet stage, a manipulation of the magnetic field of the crystal stage, a reading stage and an outlet stage. The manipulation stage is assisted by the temperature controller and the minute magnetic field source.

In an embodiment the inlet and outlet are standard microfluid channels.

In another embodiment the inlet, incubation and manipulation stages occur at a temperature where the magnetic field of the magnetic crystal is small enough such that its direction can be changed by a minute magnetic field.

In an embodiment the manipulation stage comprises the application of a small magnetic field and a temperature change such that the magnetic field created by the probe element increases and is set fixed with a defined direction and intensity.

In another embodiment the temperature change and small magnetic field created at the manipulation stage are assisted by the temperature controller and the minute magnetic field source respectively.

In an embodiment the analyte determination is based on the detection by the reader of the magnetic field created by the magnetic crystal, after the manipulation stage.

In another embodiment the reading stage comprises the determination of the remanent magnetic field created by the magnetic crystal of the probe element by a magnetic field reader.

In an embodiment the reading stage is made in the absence of an external field, at a temperature different from that used during the inlet and incubation stages.

The present application further includes a process for selective separation of analytes comprising:
- the capture of analytes using probe elements;
- the application of a magnetic field gradient using the magnetic field source at a well-defined temperature;
- The probe elements have temperature dependent remanent magnetization and magnetic susceptibility that controls the separation velocity.

In an embodiment the different probe elements have magnetic crystals with different remanent magnetizations and different temperature dependencies.

In another embodiment this process is used together with the first process as a pre or post process.

In another embodiment it is mediated by a positioning system and a tip, where temperature at the tip can be controlled.

In another embodiment it is used as a stand-alone method when analyte determination is not mandatory.

DISCLOSURE

The present application discloses a probe element that can be used for separation and sensing of analytes of interest in the absence of an external field, without aggregation of the probe element. This is, the probe elements and the analyte can be anchored together and the probe elements can carry a permanent field that can be sensed by a magnetic field reader. The intensity of the permanent field of the probe element is controlled by temperature and therefore, aggregation and sensitivity are also controlled by temperature.

The probe elements provided herein include at least one magnetic crystal and at least one type of capping agent.

BRIEF DESCRIPTION OF DRAWINGS

For an easier understanding of this application, figures are attached in the annex that represent the preferred forms of implementation which nevertheless are not intended to limit the technique disclosed herein.

DESCRIPTION OF EMBODIMENTS

Now, preferred embodiments of the present application will be described in detail with reference to the annexed drawings. However, they are not intended to limit the scope of this application.

Figure 1A:
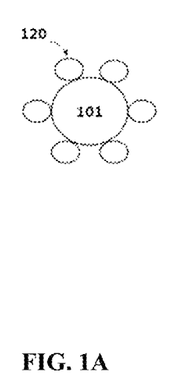
FIG. 1A depicts one embodiment of a probe element, composed of a magnetic crystal (101) and capping agents (120).

The magnetic crystal (101) is designed as such that the permanent magnetic field that it is able to create is controlled by temperature, within a temperature range compatible with the integrity of the analyte of interest. Within this temperature range, two distinct situations can be achieved: one, at a given temperature, the permanent field of the magnetic crystal is small enough to avoid aggregation and to avoid separation by a magnetic field gradient and two, at another given temperature, the permanent field of the magnetic crystal is high enough to be detected and separated by a magnetic field gradient.

In an embodiment the analytes of interest are molecules that maintain their integrity and reversibility of all their relevant properties within a temperature range between 4 and 100° C. In other embodiments this temperature range is 4 to 60° C.

In an embodiment, the magnetic crystal is composed of at least one nanoparticles with a composition and structure chosen such that its remanent magnetization decreases sufficiently within the temperature range between 5 and 60° C. In one embodiment, the composition includes at least one transition metal atom or ion. In another embodiment, the composition includes at least one lanthanide atom or ion. In another example, the composition includes at least one of the previous ions and one ion of group 16 or 17 of the periodic table. In another embodiment, the composition includes iron and selenium.

Figure 1B:
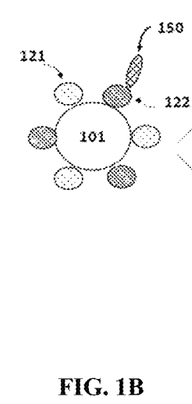
FIG. 1B depicts one embodiment of a probe element, composed of a magnetic crystal (101), capping agents behaving as stabilizers (121), capping agents behaving as anchors (122) and an analyte of interest (150).

In an embodiment, the magnetic crystal is such that at a temperature of use between −80 and 100° C. it produces a permanent magnetic field (it has a remanent magnetization) that can be sensed when the magnetic crystal is at a temperature higher than 100° C. but still at a temperature such that the analyte of interest maintains its integrity, this permanent field is substantially reduced. As an embodiment, the magnetic crystal is composed of iron selenide ($Fe_3Se_4$) with a remanent magnetization of 0.3 emu/g at 25° C. being reduced to 0 emu/g at 50° C., as shown in FIG. 1D. As another embodiment, the substantial reduction of the permanent magnetic field of the magnetic crystal above the temperature of interest allows an easy manipulation of the direction of this crystal's magnetic field by a minute external field with an amplitude from 0.1 to 1000 Oe.

Figure 1C:
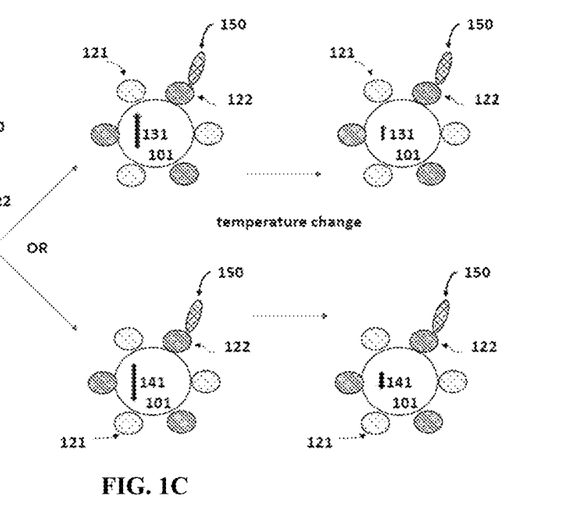
FIG. 1C depicts one embodiment of a probe element, where the magnetic crystal (101) provides a permanent magnetic field in the up (131) or down (141) direction, whose intensity is changeable with temperature.
Figure 1D:
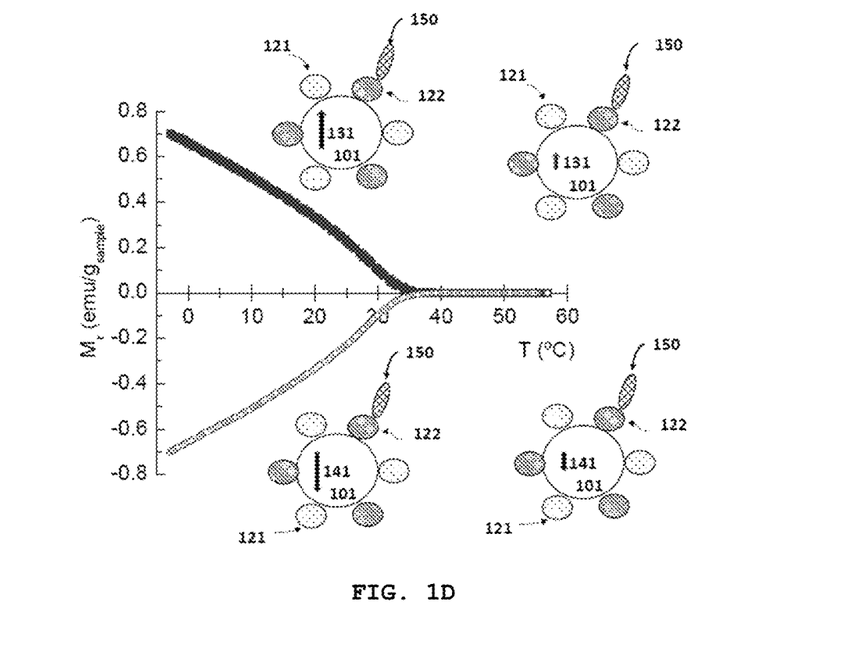
FIG. 1D depicts the permanent (remanent) magnetization created by the magnetic crystal FeSe in the up (131) and down (141) direction as a function of temperature.
Figure 1E:
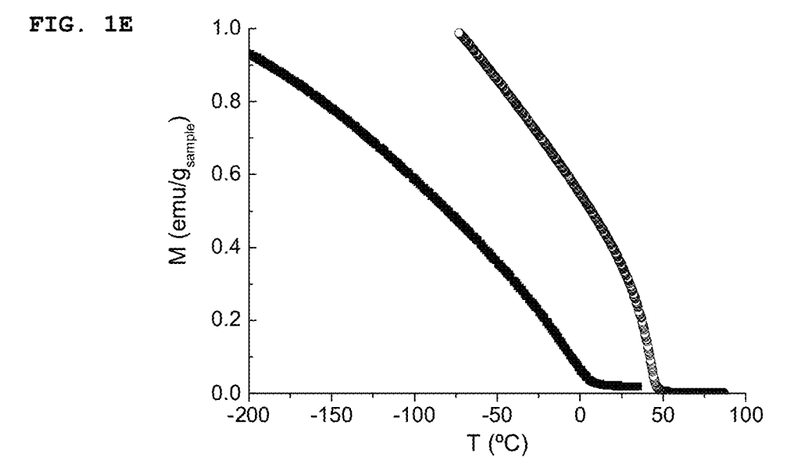
FIG. 1E depicts the permanent (remanent) magnetization of two different magnetic crystals designed to work in two complementary temperature regions (one from −200° C. to 40° C.) and the other from −75° C. to 90° C.).
Figure 1F:
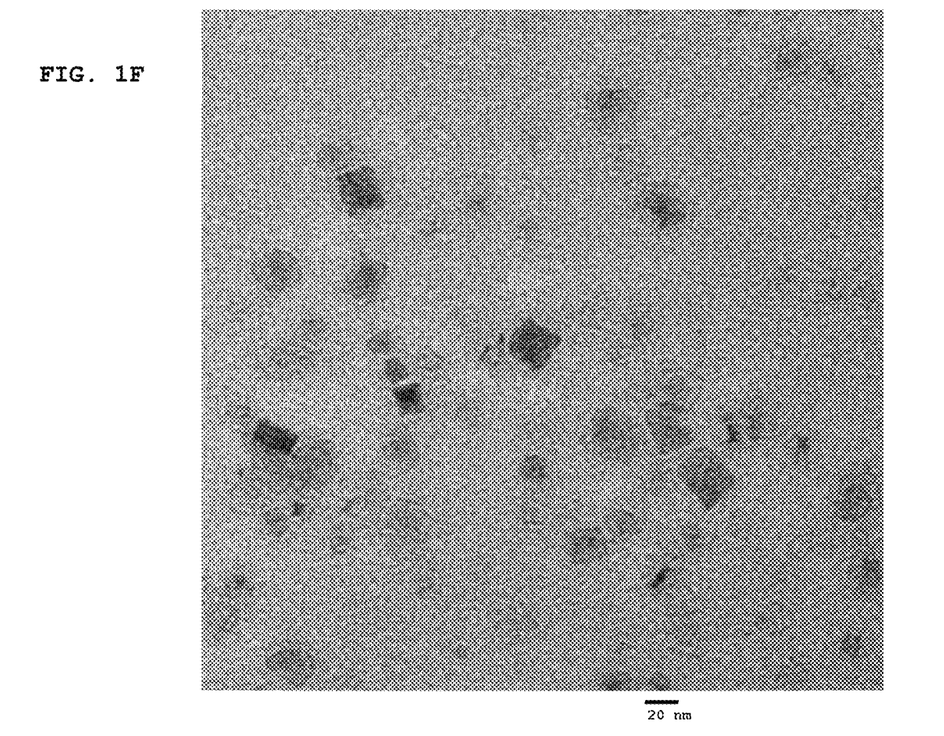
FIGS. 1F and 1G depict electron microscope images of magnetic crystals of $Fe_3Se_4$ with sizes ranging from 5 nm to 500 nm.
Figure 1G:
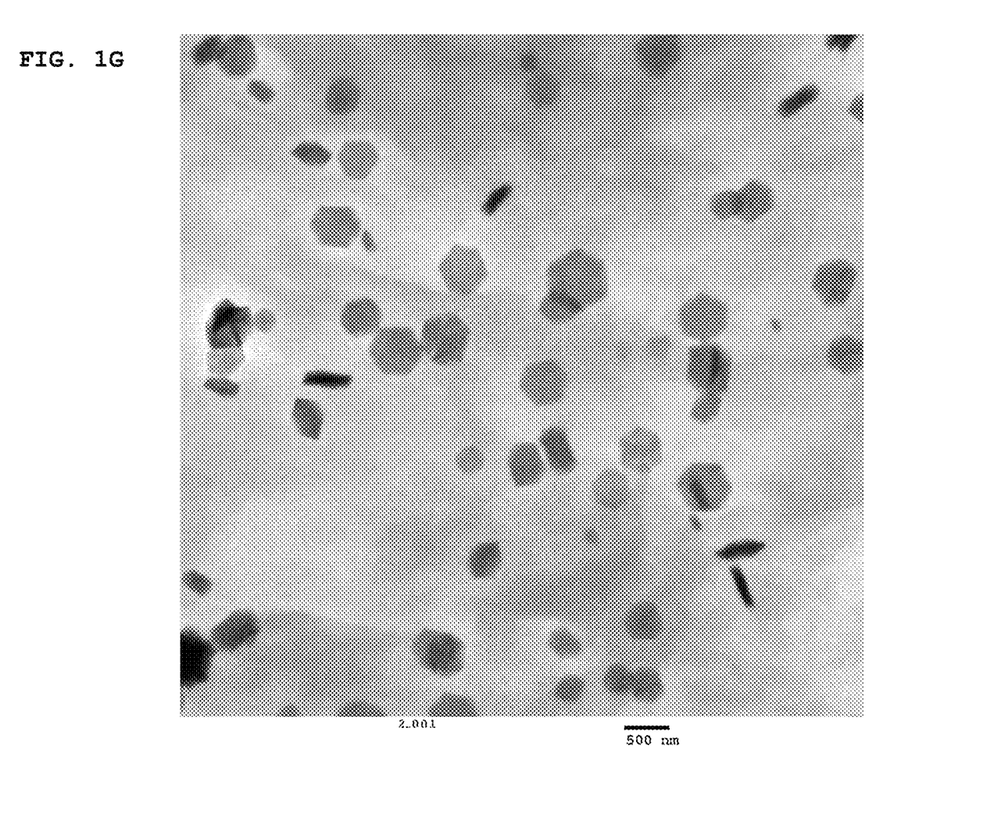

The temperature of use is defined between −80 and 100° C., preferably between 4 and 100° C., more preferably between 4 and 60° C., as shown in figure FIG. 1E.

In an embodiment, the magnetic crystal is composed of one or more nanoparticles with a well-defined shape and with size ranging from 5 to 500 nm. In a particular embodiment, the magnetic crystal is composed of $Fe_3Se_4$ nanoparticles with size between 50 and 400 nm. In another embodiment, the magnetic crystal is composed of $Fe_3Se_4$ nanoparticles with size between 100 and 200 nm.

In an embodiment, the probe element has a second magnetic crystal that does not produce a magnetic field in the absence of an external field at a temperature of use.

In another embodiment, this second magnetic crystal is used to produce an extra response in the presence of an external magnetic field, constant in the temperature range of interest. In another embodiment, this second magnetic crystal is used to generate heat by the application of an external alternating magnetic field. In an embodiment, the second magnetic crystal is magnetite. In another embodiment, the second magnetic crystal is a ferrite.

The capping agent (120) is designed to interface the magnetic crystal and the surrounding media. In this view, the capping agent can include a wide range of possibilities designed for a particular application, from simple termination groups of the magnetic crystal to large molecules and composites. The capping agents can be an organic molecule/coating, an inorganic coating/molecule or an organic-inorganic coating.

In an embodiment, the capping agent (121) is such that the probe element is stable in the carrying fluid of interest at least in a temperature within the temperature range compatible with the integrity of the analyte of interest. In an embodiment, the capping agent is the gallic acid and the fluid of interest is water or an aqueous buffer with pH between 3 and 10. In another embodiment, the capping agent is caffeic acid in similar conditions, allowing further functionalization with a molecule containing a reactive group such as an Amine (—NH2), an Hydroxyl (—OH) or a Thiol (—SH) group. In another embodiment, the caffeic acid is functionalized by a polymer containing an Amine or Thiol as a terminal functional group.

In another embodiment, the capping agent is Levodopamine in similar conditions, allowing further functionalization with a molecule containing a reactive group such as carboxylic (—COOH), Amine (—NH2), hydroxyl (—OH) or a Thiol (—SH) group. In another embodiment, the capping agent is obtained after hydrolysis and condensation of alkoxysilanes such as tetraethoxysilane or other organosilanes. Mixtures of different capping agents are also of interest such as but not restricted to, the gallic acid and an amine-functionlized organosiliceouse precursor such as (3-Aminopropyl)triethoxysilane.

In an embodiment, the capping agent (122) is such that the probe element is able to produce a luminescent signal that can be externally detected. In an embodiment, the capping agent contains rare-earth complexes such as Eu3+ beta-diketones. In another embodiment, the capping agent contains carbon dots.

In an embodiment, the capping agent (122) is such that the luminescent signal can be used to sense temperature at the probe element and in its surroundings, by a ratio of intensities of by a change in the life-time of the luminescence. In an embodiment, the capping agent contains a mixture of rare-earth complexes such as Eu3+ and Tb3+ beta-di-ketones.

In an embodiment, the capping agent (122) is such that the probe element is able to anchor analytes of interest. As an example, the capping agent is the gallic acid and the analyte of interest (150) is a molecule with an amine group. Although other types of reaction between the probe and the analyte can also be used, another embodiment includes dopamine as the capping agent and the analyte of interest is a molecule with a carboxyl group.

In an embodiment, the ratio between the magnetic crystal and capping agent ranges from 1% to 90% in mass.

One embodiment of a probe element is depicted in FIG. 1A, and includes a magnetic nanocrystal (101) and a capping agent (120). The other embodiment of a probe element depicted in FIG. 1B, includes further a capping agent (121) acting as a stabilizer and a second capping agent (122) acting as an anchor for the analyte of interest (150).

One embodiment of a probe element is depicted in FIG. 1C, and includes a magnetic nanocrystal (101) that is able to provide a magnetic field (131) with a well-defined direction and a magnetic field (141) with the opposite direction. In this embodiment of a probe element, the intensity of the magnetic fields (131) and (141) depends on temperature and can be reduced by a temperature change. In one embodiment, the change with temperature of the intensity of the magnetic fields (131) and (141) is expressed by the change with temperature of the remanent magnetization as depicted in FIG. 1D.

The device provided herein is composed of at least one probe element, at least one analyte of interest, at least one temperature controller, at least one magnetic field reader, and at least one minute magnetic field source.

Figure 2:
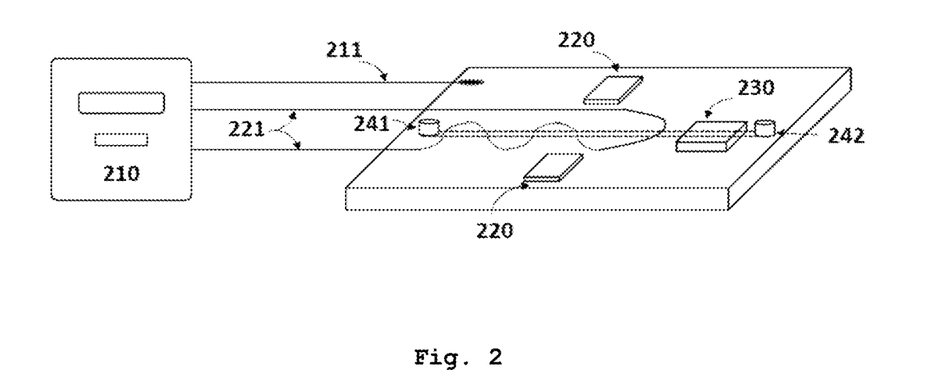
FIG. 2 depicts one embodiment of a device, where temperature control is provided by a Proportional-integral (PI) or a Proportional-integral-derivative (PID) controller (210), a temperature sensor (211), a peltier (or heater) unit (212), a magnetic field source composed of permanent magnets (220), a (fluxgate) magnetic field sensor (230), an inlet (241) and an outlet (242).

One embodiment of a device is depicted in FIG. 2, and includes a 3-state temperature controller unit (210), a temperature sensor (211), a peltier heating/cooling unit (212), a magnetic field source (220) composed of permanent magnets, a magnetic field reader (230), an inlet (241) and an outlet (242) unit.

In one embodiment, the device is designed such that the minute magnetic field source is sufficiently far and shielded from the magnetic field reader such they do not interact. In another embodiment, at the time where reading takes place, the magnetic field source is off, such they do not interact during reading.

In one embodiment, the device is designed such that the temperature controller is able to control temperature across the device within the temperature range of interest. In another embodiment, the temperature controller includes a feedback and/or feedforward controller such as PI or a PID unit, a temperature sensor and an external heating element such as a resistance.

In another embodiment, the heating element is internal, i.e., it is the probe element itself that is able to absorb energy from an external source and convert this energy into heat. As an embodiment, the external source is a laser and absorption is made by the magnetic crystal. As another embodiment, the external source is an alternate magnetic field and absorption is made by the magnetic crystal.

In one embodiment the device is designed such that the magnetic field source is a miniaturized field source composed of permanent magnets. These magnets may further have a magnetic field circuit to guide the magnetic field lines. In another embodiment, the magnetic field source is a miniaturized field source composed of a coil at a distance from the magnetic field reader used together or not with the permanent magnet. In another embodiment, the coil is embedded in the magnetic field reader.

In an embodiment, the magnetic field reader (230) can be based on a magnetoresistive sensor, on fluxgate sensors, on miniaturized fluxgate sensors, on hall sensors, on squid sensors, on magnetic force microscopy, or any other sensor used to detect magnetic fields. In another embodiment, the magnetic field reader is shielded from the magnetic field sources using, for example, a high permeability tin foil.

In an embodiment, the magnetic crystal of the probe element is coupled or embedded in the magnetic field reader. In an embodiment, the probe element is used embedded in the tip of a magnetic force microscope. In another embodiment, the probe element is used coupled to the tip of a magnetic force microscope.

In an embodiment, the analyte of interest is a Cell, maintaining its integrity up to 42° C. In another embodiment, the analyte of interest is a cancer or a pathogenic cell. In an embodiment, the analyte of interest is a relevant cell biomarker such as proteins or polypeptides maintaining its integrity up to 60° C. In an embodiment, the analyte of interest is a cardiac biomarker, such as cardiac troponin T, CK-MB or colon cancer biomarker such as Calcitonin, maintaining integrity up to 60° C.

In another embodiment, the analyte of interest is a cell biomarker such as nucleic acids or nucleic acid sequences, maintaining their integrity up to 60° C. In an embodiment, the analyte of interest is a RNA or DNA sequence for detection of a pathogen (Salmonella).

In an embodiment, the analyte of interest is a microRNA sequence for breast cancer detection.

In an embodiment, the composite contains an Aptamer for thrombin detection.

In another embodiment, the analyte of interest is an exosome/vesicle, the analyte of interest is a biomarker for cancer detection.

In another embodiment, the analyte of interest is a cell biomarker such as an organic molecule. In another embodiment, the analyte of interest is a hormone such as Thyroid-stimulating hormone (TSH) for hypothyroidism detection. In an embodiment, the analyte of interest is a small organic molecule such as 5-hydroxyindoleacetic acid for Alzheimer's disease diagnosis.

In another embodiment, the analyte of interest is a cell biomarker and it is detected by a composite that includes one or more synthetic biomolecules, such as a Xeno Nucleic acid, a Peptide Nucleic Acid (PNA), or a Locked Nucleic Acid (LNA) or a Peptoid.

In another embodiment, the analyte of interest is a cell biomarker and it is detected by a composite that includes another nanoparticle or a molecular cluster. As an embodiment, a Sandwich assay between a magnetic nanoparticle and an optically active nanoparticle or a polymeric nanoparticle.

In another embodiment, the analyte of interest is a cell biomarker such as an inorganic molecule. As an embodiment, the analyte is the detection of nitric oxide (NO) as a biomarker for a bowel inflammatory disease.

The process provided herein includes an inlet stage, a proper manipulation of the magnetic field of the crystal stage; a reading stage and an outlet stage.

In one embodiment, the inlets and outlets are standard microfluid channels. In another embodiment, the inlets and outlets are made of a polymer or made of an organosilicon material.

In an embodiment, the inlet, incubation and manipulation stages occur at a temperature where the magnetic field of the magnetic crystal is small, such that aggregation of the probe element does not occur, and said temperature is within a range that maintains intact and reversible the relevant properties of the analyte of interest. In another embodiment, aggregation of the probe element may occur after incubation and manipulation stages, at a lower temperature where the magnetic crystal creates a relevant magnetic field; in this sense, aggregation of the probe element is controlled by the magnetic field created by the crystal, which in turn is controlled by temperature.

In an embodiment, the manipulation stage comprises the application of a small magnetic field and a temperature change such that the magnetic field created by the probe element increases and is set fixed with a defined direction and intensity. The temperature change and small magnetic field created at the manipulation stage are assisted by the temperature controller and the minute magnetic field source, respectively.

In another embodiment, the magnetic field is in the 0.5 to 100 Oe range and the temperature change in the 1 to 60° C. range.

In an embodiment, the reading stage comprises the determination of the remanent magnetic field created by the magnetic crystal of the probe element by a magnetic field reader.

In an embodiment, the reading stage is made in the absence of an external field, at a temperature different from that used during the inlet and incubation stages, since the magnetic field created by the probe element is stable and aggregation is not a problem at this stage.

The process provided herein can have a second process used to separate and/or increase the concentration of the analyte or the analytes of interest, before the inlet stage, after the outlet stage or in between stages, using a temperature controller and a magnetic field source, as described in previous embodiments.

In one embodiment, this second process involves the application of a magnetic field gradient, using the magnetic field source, at a well-defined temperature, determined by the temperature controller, where the probe element has a given remanent magnetization and magnetic susceptibility that controls the separation velocity.

In one embodiment, analyte determination is not necessary and separation and/or concentration increase is used as a stand-alone process where the separation velocity is controlled by temperature, via the temperature dependent remanent magnetization and magnetic susceptibility of the magnetic crystal of the probe element.

In one embodiment, the remanent magnetization and magnetic susceptibility are low, such that velocity is close to zero, while in another embodiment the remanent magnetization and magnetic susceptibility are high, such that velocity is between zero and 5 cm/s.

In one embodiment, this second process involves the use of different probe elements with different magnetic crystals and capping agents, such that each type of capping anchors to a different analyte and the magnetic crystals have different remanent magnetization and magnetic susceptibility such that the velocities of the probe elements under a given magnetic field gradient and at a given temperature are different. In this embodiment, the analytes can be concentrated and/or separated by using different temperatures and/or outlets placed at different distances from the magnetic field gradient, as depicted in the part of the device shown in FIG. 3.

Figure 3:
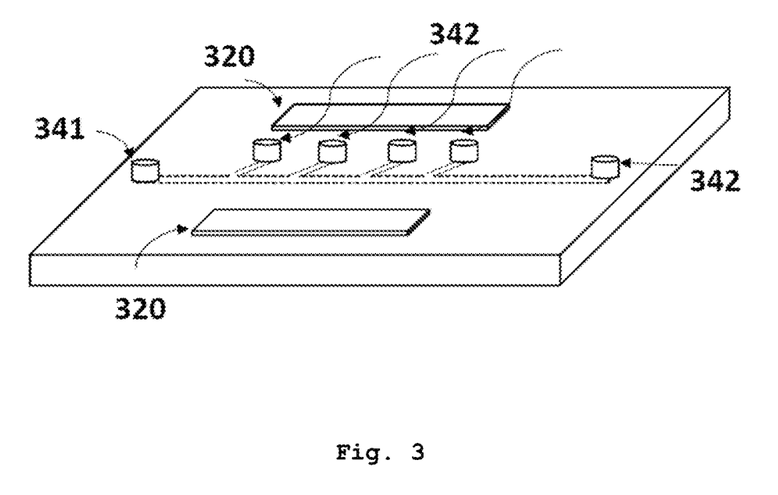
FIG. 3 depicts one embodiment of a part of the device, where separation and/or concentration occurs at different outlet systems (342), after entering at inlet (341), being exposed to a magnetic field source (320) and to a controlled temperature environment.
Figure 4A:
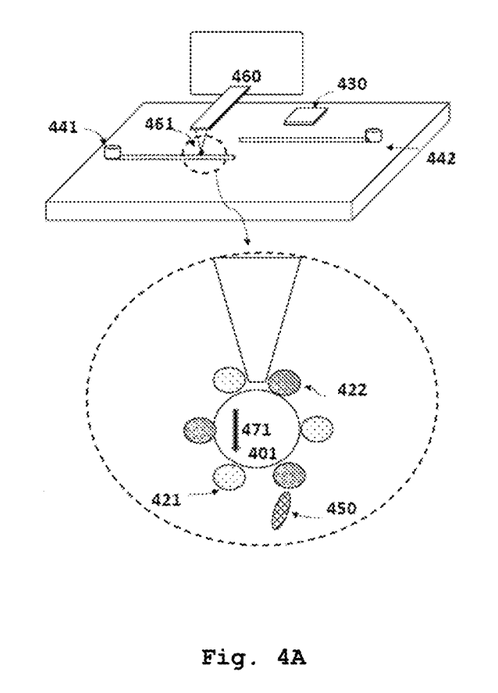
FIG. 4A depicts one embodiment of a part of the device, in a first stage of operation where separation and/or concentration and/or detection is mediated by a positioning/temperature control system (460) with a tip (461) where the probe element (401) is permanently attached to the tip or enters the inlet system (441) and attaches to the tip by magnetic forces, due to the remanent moment (471). The magnetic field source (430) is used to control the direction of magnetization of the probe element (401) and/or tip (461).
Figure 4B:
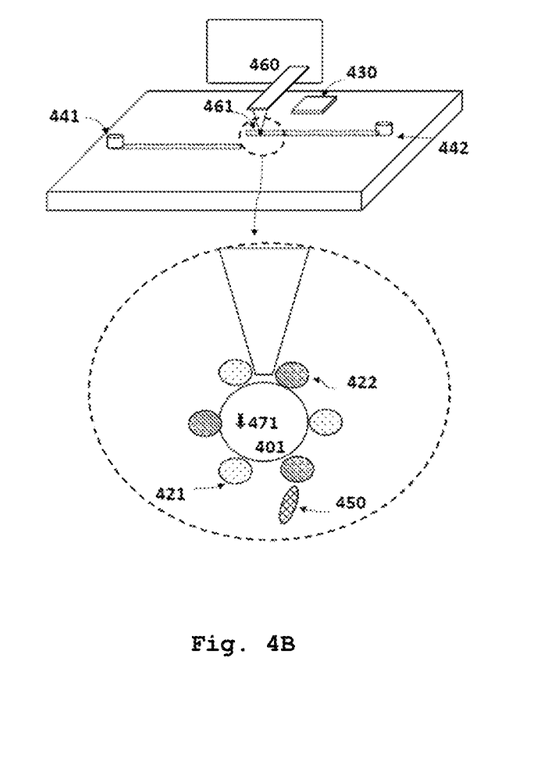
FIG. 4B depicts the same embodiment of FIG. 4A in a second stage of operation where the probe element (401) and/or analyte of interest (450) is detached from the tip (461) by a change in temperature and consequent reduction of remanent magnetization (471). Element (421) depicts capping agents and element (122) depicts capping agents behaving as anchors.

In one embodiment, this second process involves the use of a general positioning system and a tip, as shown in FIG. 3. As examples of positioning systems and tips we mention atomic force microscopy devices and similar tip-based devices. As embodiments of operation we mention the following two, both involving a temperature change and control at the tip. In the first one, and in a first stage, at a given temperature, the magnetic crystal of the probe element has a remanent magnetization, such that it is able to attract other magnetic crystals from an inlet system. Said other magnetic crystals can have the same magnetic nature of the magnetic crystal of the probe element or can have other nature, such as: superparamagnetic, hard and soft ferromagnetic, hard and soft ferrimagnetic, spin glasses and mixtures of the previous. In a second stage, at another given temperature, the remanent magnetization of the magnetic crystal of the probe element is reduced, such that attraction between the probe element and the other magnetic crystal is no longer enough to sustain both together and the other magnetic crystal and all elements attached to it can be dropped and counted at an outlet stage.

As a second embodiment of operation, we mention the use of the tip of said microscopy device containing the other magnetic crystal, with the above detailed properties, and the use of the probe element as the element to be collected, separated, counted and/or dropped in an outlet stage. The operation of this second embodiment is similar to the first one, except that the positions of the probe element and of the other magnetic crystal are swapped.

This description is of course not in any way restricted to the forms of implementation presented herein and any person with an average knowledge of the area can provide many possibilities for modification thereof without departing from the general idea as defined by the claims. The preferred forms of implementation described above can obviously be combined with each other. The following claims further define the preferred forms of implementation.

REFERENCES

[1] S. Wang X, R. L. White, C. D. Webb, and G. Li, *Magnetic nanoparticles, magnetic detector arrays, and methods for their use in detecting biological molecules* (2011), http://www.freepatentsonline.com/7906345.html.

[2] J. A. H. M. Kahlman and M. W. J. Prins, *On-chip magnetic particle sensor with improved snr* (2005), http://www.freepatentsonline.com/WO2005010542.html.

[3] S. Wang X, S. J. Osterfeld, H. Yu, N. Pourmand, and R. L. White, *Analyte detection with magnetic sensors* (2009), http://www.freepatentsonline.com/y2009/0104707b820.html.

[4] P.-k. Wang, Y. Guo, C. Horng, T. Min, and R.-y. Tong, *Mram with super-paramagnetic sensing layer* (2010), http://www.freepatentsonline.com/7696548.html.

[5] G. A. Prinz and M. M. Miller, *High efficiency magnetic sensor for magnetic particles* (2005), http://www.freepatentsonline.com/6844202.html.

[6] J.-p. Wang, C. Xing, Y. Li, and B. Srinivasan, *High magnetic moment particle detection* (2015), http://www.freepatentsonline.com/9121887.html.

[7] D. L. Graham, H. A. Ferreira, and P. P. Freitas, Trends in Biotechnology 22, 455 (2004), ISSN 0167-7799, http://www.sciencedirect.com/science/article/pii/S01677799004001714.

[8] I. Koh and L. Josephson, Sensors 9, 8130 (2009), ISSN 1424-8220, http://www.mdpi.com/1424-8220/9/10/8130.

[9] I.-M. Hsing, Y. Xu, and W. Zhao, Electroanalysis 19, 755 (2007), ISSN 1521-4109, http://dx.doi.org/10.1002/elan.200603785.

[10] E. Palecek and M. Fojta, Talanta 74, 276 (2007), ISSN 0039-9140, micro- and Nanotechnology in Electrochemical Detection Science—dedicated to Professor Joseph Wang on the occasion of his 60th birthdayMNED 2007 {SI}, http://www.sciencedirect.com/science/article/pii/S003991400 7005723.

[11] F. Ludwig, S. Mauselein, E. Heim, and M. Schilling, Review of Scientific Instruments 76, 106102 (2005), http://scitation.aip.org/content/aip/journal/rsi/76/10/10.1063/1.2069776.

The invention claimed is:

1. A probe element comprising:
at least a first magnetic crystal and a second magnetic crystal, and
at least one type of capping agent,
wherein the first magnetic crystal provides a controllable temperature dependent remanent magnetization creating a controllable magnetic field to be sensed,
wherein the second magnetic crystal does not produce a magnetic field in the absence of an external field at a temperature of use, and
wherein the second magnetic crystal generates heat by the application of an external alternating magnetic field.

2. The probe element according to claim 1, wherein the first magnetic crystal produces a magnetic field in the absence of an external field at a temperature of use.

3. The probe element according to claim 1, wherein the first magnetic crystal further produces a magnetic field in a well-defined direction and in its opposite direction.

4. The probe element according to claim 1, wherein the intensity of the magnetic field produced by the first magnetic crystal changes by a temperature change.

5. The probe element according to claim 1, wherein aggregation of the probe element is controlled by the magnetic field created by the first magnetic crystal of the probe element, which in turn is controlled by temperature change.

6. The probe element according to claim 1, wherein the at least one type of capping agent is an anchoring agent.

7. The probe element according to claim 1, wherein the at least one type of capping agent is a stabilizing agent.

8. The probe element according to claim 1, wherein the at least one type of capping agent is selected from the group consisting of: organic molecules/coatings, inorganic molecules/coatings, organic-inorganic coatings and a mixture thereof.

9. The probe element according to claim 1, wherein the at least one type of capping agent is luminescent.

10. A device comprising at least one probe element described in claim 1, at least one analyte of interest, at least one temperature controller, at least one magnetic field reader, and at least one minute magnetic field source, wherein said at least one minute magnetic field source does not interact with the said at least one magnetic field reader.

11. The device, according to claim 10 wherein the at least one analyte of interest is selected from the group consisting of: cells, cell biomarkers, synthetic biomarkers, synthetic biomarkers composites, biomolecules, exosomes, vesicles, organic molecules, inorganic molecules, molecular clusters, nanoparticles.

12. The device according to claim 10, wherein the at least one temperature controller comprises a heating element, a temperature sensor, and a feedback and/or feedforward controller.

13. The device according to claim 12, wherein the heating element is the at least one probe element that absorbs energy from an external source and converts this energy into heat.

14. The device according to claim 10, wherein the at least one probe element is coupled or embedded into the at least one magnetic field reader.

15. The device according to claim 10, wherein the at least one magnetic field reader is a fluxgate sensor.

16. The device according to claim 15, wherein the fluxgate sensor is a miniaturized unit.

17. The device according to claim 10, wherein the at least one magnetic field reader is a magnetoresistive sensor.

18. The device according to claim 10, wherein the at least one magnetic field reader is a tip-based device.

19. The device according to claim 18, wherein the tip-based device is an atomic force device.

20. The device according to claim 19, wherein a tip of the atomic force device comprises a magnetic crystal.

21. The device according to claim 10, wherein the at least one minute magnetic field source is a coil at a distance from the reader.

22. The device according to claim 10, wherein the at least one minute magnetic field source is a permanent magnet at a distance from the reader.

23. The device according to claim 10, wherein the at least one minute magnetic field source is embedded in the at least one magnetic field reader.

24. The device according to claim 10, wherein the at least one magnetic field reader is at a distance from a shielded magnetic field source.

25. A process for selective separation of analytes comprising:
capturing analytes using probe elements, each probe element comprising a probe element as described in claim 1; and applying a magnetic field gradient using the magnetic field source at a well-defined temperature;

wherein the probe elements have temperature dependent remanent magnetization and magnetic susceptibility that control a separation velocity.

26. The process of selective separation according to claim 25, wherein different probe elements have magnetic crystals with different remanent magnetizations and different temperature dependencies.

27. The process for selective separation according to claim 25, wherein the process for selective separation of analytes is used together with a first process as a pre-process or post process.

28. The process for selective separation according to claim 25, further comprising mediating the process for selective separation by a positioning system and a tip, where temperature at the tip can be controlled.

29. The process for selective separation according to claim 25, wherein the process for selective separation of analytes is used as a stand-alone method.

* * * * *